(12) United States Patent
Gibson et al.

(10) Patent No.: US 9,146,210 B2
(45) Date of Patent: Sep. 29, 2015

(54) CONTROL SYSTEM AND METHOD FOR HEATING AN OXYGEN SENSOR

(76) Inventors: Bradley Gibson, Swartz Creek, MI (US); Michael L. Kociba, Hartland, MI (US); Eric M. Hall, Rochester Hills, MI (US)

( * ) Notice: Subject to any disclaimer, the term of this patent is extended or adjusted under 35 U.S.C. 154(b) by 864 days.

(21) Appl. No.: 12/917,868

(22) Filed: Nov. 2, 2010

(65) Prior Publication Data
US 2012/0102917 A1     May 3, 2012

(51) Int. Cl.
| | |
|---|---|
| F01N 3/00 | (2006.01) |
| F01N 3/02 | (2006.01) |
| F01N 3/10 | (2006.01) |
| F01N 3/20 | (2006.01) |
| G01N 27/406 | (2006.01) |

(52) U.S. Cl.
CPC .................. G01N 27/4067 (2013.01)

(58) Field of Classification Search
USPC ............... 204/424, 425, 426; 60/272–324
See application file for complete search history.

(56) References Cited

U.S. PATENT DOCUMENTS

| | | | | |
|---|---|---|---|---|
| 4,500,412 A | * | 2/1985 | Takahashi et al. | 204/425 |
| 4,510,036 A | * | 4/1985 | Takeuchi et al. | 204/425 |
| 4,574,264 A | * | 3/1986 | Takahashi et al. | 338/34 |
| 4,694,809 A | * | 9/1987 | Nakano et al. | 123/684 |
| 5,291,673 A | * | 3/1994 | Hamburg et al. | 60/274 |
| 5,547,552 A | * | 8/1996 | Hasegawa et al. | 204/406 |
| 5,719,778 A | * | 2/1998 | Suzumura et al. | 700/207 |
| 5,827,415 A | * | 10/1998 | Gur et al. | 204/426 |
| 6,365,021 B1 | * | 4/2002 | Kano et al. | 204/426 |
| 7,611,612 B2 | * | 11/2009 | Nair et al. | 204/426 |
| 2004/0187482 A1 | * | 9/2004 | Bidner et al. | 60/285 |
| 2007/0277605 A1 | * | 12/2007 | Fouts et al. | 73/431 |
| 2009/0150057 A1 | * | 6/2009 | Adams et al. | 701/109 |
| 2009/0173326 A1 | * | 7/2009 | Aoki | 123/693 |

FOREIGN PATENT DOCUMENTS

| | | |
|---|---|---|
| CN | 101349206 A | 1/2009 |
| JP | 2001330583 A | 11/2001 |

\* cited by examiner

*Primary Examiner* — Audrey K Bradley
*Assistant Examiner* — Dapinder Singh

(57) ABSTRACT

A control system includes a temperature determination module and a heater control module. The temperature determination module determines a temperature of an oxygen sensor in an exhaust system of an engine. The heater control module applies a heat cycle to combust deposits on the oxygen sensor by activating a heating element of the oxygen sensor to increase the temperature of the oxygen sensor to greater than 800 degrees Celsius.

22 Claims, 5 Drawing Sheets

CONTROL SYSTEM AND METHOD FOR HEATING AN OXYGEN SENSOR

FIELD

The present disclosure relates to oxygen sensors and exhaust systems of engines, and more particularly to control systems and methods for heating the oxygen sensors.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Internal combustion engines combust a mixture of air and fuel to produce torque. Exhaust gas resulting from the combustion is passed through an exhaust system before exiting to the atmosphere. Typically, the exhaust system includes an oxygen sensor that measures oxygen levels in the exhaust gas. An air/fuel (A/F) ratio of the engine is determined based on the oxygen levels, and the engine is controlled based on the A/F ratio.

Over time, particles from the exhaust gas may build up on an oxygen sensor, increasing the response time of the oxygen sensor. The response time of an oxygen sensor is the amount of time that elapses after a change in the A/F ratio before the oxygen sensor responds to the change in the A/F ratio. Eventually, deposits on the oxygen sensor may completely diminish the ability of the oxygen sensor to detect oxygen. The oxygen sensor may be replaced when the response time exceeds an acceptable limit or when the ability of the oxygen sensor to detect oxygen is completely diminished.

SUMMARY

A control system includes a temperature determination module and a heater control module. The temperature determination module determines a temperature of an oxygen sensor in an exhaust system of an engine. The heater control module applies a heat cycle to combust deposits on the oxygen sensor by activating a heating element of the oxygen sensor to increase the temperature of the oxygen sensor to greater than 800 degrees Celsius.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
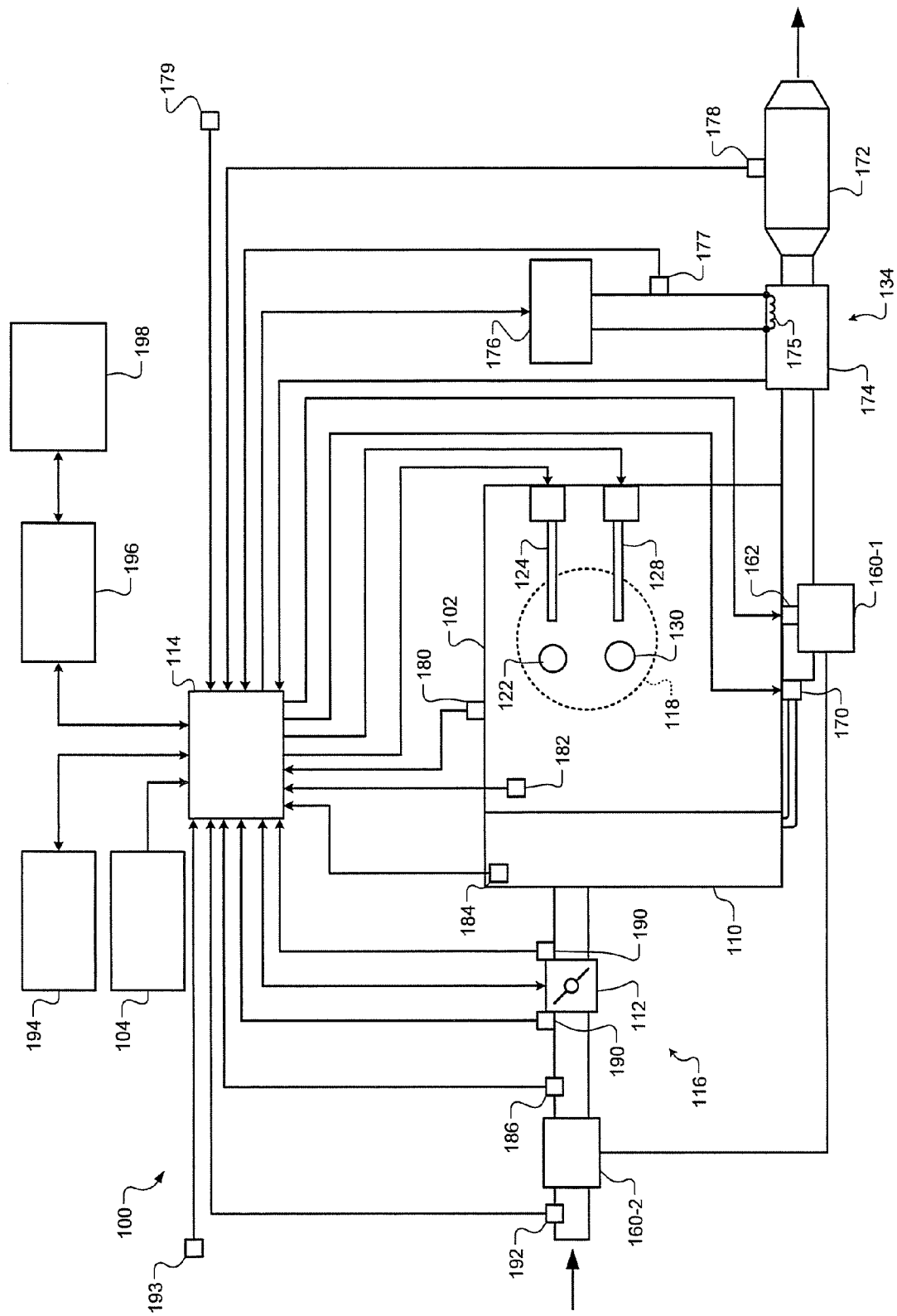
FIG. 1 is a functional block diagram of an example of an engine system according to the principles of the present disclosure.

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

An exhaust system of an engine typically includes an oxygen sensor to determine an air/fuel (A/F) ratio of the engine. An oxygen sensor typically includes a ceramic structure and a heating element on or within the ceramic structure. The ceramic structure includes microscopic pores through which oxygen ions flow. The oxygen sensor generates a voltage that is proportional to the amount of oxygen ions flowing through the pores.

A catalytic converter is most efficient at reducing emissions when the A/F ratio is at or near stoichiometric. Thus, the oxygen sensor provides feedback to enable closed-loop control of the A/F ratio. When an engine is initially started, the response time of the oxygen sensor is insufficient for closed-loop control of the A/F ratio until the oxygen sensor is heated to an activation temperature. Typically, the activation temperature is approximately 300 degrees Celsius (° C.), or approximately 572 degrees Fahrenheit (° F.).

When an engine is started, several minutes may elapse before exhaust gas heats the oxygen sensor to this activation temperature. Thus, the heating element is used to increase the temperature of the oxygen sensor faster than may be achieved using the exhaust gas heat only. The heating element may be controlled to a fixed voltage or a fixed temperature while the engine is on. A typical control range of the heating element is between 600° C. and 800° C.

During the life of an oxygen sensor, deposits from exhaust gas may plug the pores in the ceramic element of the oxygen sensor. These deposits may include carbon, phosphorous, silicone, sulfur, zinc, lead, manganese, and/or calcium. The buildup of deposits in the pores of the oxygen sensor inhibits the ability of the oxygen sensor to flow oxygen ions through the pores. In turn, the response time of the oxygen sensor increases. The response time of an oxygen sensor is the amount of time that elapses after a change in the A/F ratio of an engine before the oxygen sensor responds to the change in the A/F ratio. An oxygen sensor may be replaced when its response time exceeds an acceptable limit.

A control system and method according to the principles of the present disclosure employs a reactive approach and a proactive approach to maintain the response time performance of an oxygen sensor. In the reactive approach, a heat cycle is applied to combust deposits in or on the oxygen sensor. In the proactive approach, a heat cycle is periodically applied to prevent the buildup of deposits on the oxygen sensor. Applying a heat cycle may include heating the oxygen sensor to a predetermined temperature and/or for a predetermined period. The predetermined temperature may be greater than a typical control range of the heating element (e.g., greater than 800° C.).

Maintaining the performance of the oxygen sensor in this manner decreases the number of times that an oxygen sensor must be replaced. In turn, replacement costs are reduced and customer satisfaction is improved. In addition, maintaining the performance of the oxygen sensor in this manner may be particularly beneficial to vehicles with infrequent high temperature operation, such as hybrids with start/stop and/or extended range functions. Applying a heat cycle may be the only way to prevent the buildup of deposits in these vehicles.

Referring now to FIG. 1, a functional block diagram of an exemplary engine system 100 is presented. The engine system 100 includes an engine 102 that combusts an A/F mixture to produce drive torque for a vehicle based on driver input from a driver input module 104. Air is drawn into an intake manifold 110 through a throttle valve 112. For example only, the throttle valve 112 may include a butterfly valve having a rotatable blade. An engine control module (ECM) 114 regulates opening of the throttle valve 112 to control the amount of air drawn into the intake manifold 110. An intake system 116 includes the intake manifold 110 and the throttle valve 112.

Air from the intake manifold 110 is drawn into cylinders of the engine 102. While the engine 102 may include multiple cylinders, for illustration purposes a single representative cylinder 118 is shown. For example only, the engine 102 may include 2, 3, 4, 5, 6, 8, 10, and/or 12 cylinders. The ECM 114 may selectively deactivate some of the cylinders, which may improve fuel economy under certain engine operating conditions.

The engine 102 may operate using a four-stroke cycle. The four strokes, described below, are named the intake stroke, the compression stroke, the combustion stroke, and the exhaust stroke. During each revolution of a crankshaft (not shown), two of the four strokes occur within the cylinder 118. Therefore, two crankshaft revolutions are necessary for the cylinder 118 to experience all four of the strokes.

During the intake stroke, air from the intake manifold 110 is drawn into the cylinder 118 through an intake valve 122. The ECM 114 controls a fuel injector 124 to regulate fuel injection to achieve a desired A/F ratio. Fuel may be injected into the intake manifold 110 at a central location or at multiple locations, such as near the intake valve 122 of each of the cylinders. In various implementations (not shown), fuel may be injected directly into the cylinders or into mixing chambers associated with the cylinders. The fuel ECM 114 may halt injection of fuel to cylinders that are deactivated.

The injected fuel mixes with air and creates an A/F mixture in the cylinder 118. During the compression stroke, a piston (not shown) within the cylinder 118 compresses the A/F mixture. The engine 102 may be a compression-ignition engine, in which case compression in the cylinder 118 ignites the A/F mixture. Alternatively, the engine 102 may be a spark-ignition engine, in which case the ECM 114 energizes a spark plug 128 in the cylinder 118, which ignites the A/F mixture. The spark timing may be defined relative to the time when the piston is at its topmost position, referred to as top dead center (TDC).

The ECM 114 may control the spark timing based on how far before or after TDC the piston is positioned. Because piston position is directly related to crankshaft rotation, operation of the spark plug 128 may be synchronized with crankshaft angle. In various implementations, the ECM 114 may halt provision of spark to deactivated cylinders.

Generating the spark may be referred to as a firing event. The ECM 114 may have the ability to vary the spark timing for each firing event. The ECM 114 may even be capable of varying the spark timing for a next firing event when the spark timing signal is changed between a last firing event and the next firing event.

During the combustion stroke, the combustion of the A/F mixture drives the piston down, thereby driving the crankshaft. The combustion stroke may be defined as the time between the piston reaching TDC and the time at which the piston returns to bottom dead center (BDC).

During the exhaust stroke, the piston begins moving up from BDC and expels the byproducts of combustion through an exhaust valve 130. The byproducts of combustion are exhausted from the vehicle via an exhaust system 134.

The intake valve 122 and the exhaust valve 130 may be controlled by camshafts (not shown), which may be controlled by the ECM 114. The ECM 114 may deactivate the cylinder 118 by disabling opening of the intake valve 122 and/or the exhaust valve 130. In various other implementations, the intake valve 122 and/or the exhaust valve 130 may be controlled by devices other than camshafts, such as electromagnetic actuators.

The engine system 100 may include a boost device that provides pressurized air to the intake manifold 110. For example, FIG. 1 shows a turbocharger including a hot turbine 160-1 that is powered by hot exhaust gases flowing through the exhaust system 134. The turbocharger also includes a cold air compressor 160-2, driven by the turbine 160-1, that compresses air leading into the throttle valve 112. In various implementations, a supercharger (not shown), driven by the crankshaft, may compress air from the throttle valve 112 and deliver the compressed air to the intake manifold 110.

A wastegate 162 may allow exhaust to bypass the turbine 160-1, thereby reducing the boost (the amount of intake air compression) of the turbocharger. The ECM 114 may modulate the boost by controlling the position of the wastegate 162.

In various implementations, the ECM 114 may control a turbocharger having variable geometry and/or multiple turbochargers.

An intercooler (not shown) may dissipate some of the heat contained in the compressed air charge, which is generated as the air is compressed. The compressed air charge may also have absorbed heat from components of the exhaust system 134. Although shown separated for purposes of illustration, the turbine 160-1 and the compressor 160-2 may be attached to each other, placing intake air in close proximity to hot exhaust.

The exhaust system 134 may include an exhaust gas recirculation (EGR) valve 170 and a catalytic converter 172. The EGR valve 170 may be located upstream of the turbine 160-1 and may be controlled by the ECM 114 to redirect exhaust gas back to the intake manifold 110. The catalytic converter 172 reduces exhaust gas emissions through chemical reactions.

The oxygen levels in exhaust gas may be measured using an oxygen sensor 174. The oxygen sensor 174 may be a zirconia or titania sensor. The oxygen sensor 174 may include a ceramic element (not shown) and a heating element 175. The oxygen sensor 174 may be located upstream of the catalytic converter 172, downstream of the catalytic converter 172, or in the catalytic converter 172.

When the engine 102 is started, the performance of the oxygen sensor 174 may be insufficient for closed-loop control of the A/F ratio until the oxygen sensor 174 reaches an activation temperature, such as 300° C. or 572° F. Thus, the ECM 114 may use the heating element 175 to heat the oxygen sensor 174 faster than may be accomplished through exhaust gas heat only. The ECM 114 may heat the oxygen sensor 174 using the heating element 175 by controlling a power supply 176 to supply power to the heating element 175.

The ECM 114 may measure various operating conditions of the engine system 100 and control the engine system 100 based on the operating conditions measured. The current supplied to the heating element 175 may be measured using an ammeter or current sensor 177. The temperature of exhaust gas may be measured using a temperature sensor 178. The voltage of the engine system 100 may be measured using a voltmeter or voltage sensor 179.

The speed of the crankshaft may be measured in revolutions per minute (RPM) using an RPM sensor 180. The temperature of the engine coolant may be measured using an engine coolant temperature (ECT) sensor 182. The ECT sensor 182 may be located within the engine 102 or at other locations where the coolant is circulated, such as a radiator (not shown).

The pressure within the intake manifold 110 may be measured using a manifold absolute pressure (MAP) sensor 184. In various implementations, engine vacuum, which is the difference between ambient air pressure and the pressure within the intake manifold 110, may be measured. The mass flow rate of air flowing into the intake manifold 110 may be measured using a mass air flow (MAF) sensor 186. In various implementations, the MAF sensor 186 may be located in a housing that also includes the throttle valve 112.

The position of the throttle valve 112 may be measured using one or more throttle position sensors (TPS) 190. The ambient temperature of air drawn into the engine 102 may be measured using an intake air temperature (IAT) sensor 192. The rotational speed of a wheel (not shown) driven by the engine system 100 may be measured using a wheel speed sensor 193. The ECM 114 may use signals from the sensors to control the engine system 100.

The ECM 114 may communicate with a transmission control module 194 to coordinate shifting gears in a transmission (not shown). For example, the ECM 114 may reduce engine torque during a gear shift. The ECM 114 may communicate with a hybrid control module 196 to coordinate operation of the engine 102 and an electric motor 198.

The electric motor 198 may also function as a generator, and may be used to produce electrical energy for use by vehicle electrical systems and/or for storage in a battery. In various implementations, various functions of the ECM 114, the transmission control module 194, and the hybrid control module 196 may be integrated into one or more modules.

Each system that varies an engine parameter may be referred to as an actuator that receives an actuator value. For example, the throttle valve 112 may be referred to as an actuator and the throttle opening area may be referred to as the actuator value. Similarly, the spark plug 128 may be referred to as an actuator, while the corresponding actuator value may be the amount of spark advance relative to cylinder TDC.

Other actuators may include the fuel injector 124, the wastegate 162, and the EGR valve 170. For these actuators, the actuator values may correspond to fueling rate, boost pressure, and EGR valve opening area, respectively. The ECM 114 may control actuator values in order to cause the engine 102 to generate a desired engine output torque.

The ECM 114 may employ a reactive approach and/or a proactive approach to maintain the performance the oxygen sensor 174. In the reactive approach, the ECM 114 applies a heat cycle to combust deposits on the oxygen sensor 174 when the response time of the oxygen sensor 174 is greater than a predetermined time. In the proactive approach, the ECM 114 periodically applies a heat cycle to prevent the buildup of deposits on the oxygen sensor 174. The ECM 114 applies a heat cycle by powering the heating element 175 to heat the oxygen sensor 174 to a predetermined temperature and/or for a predetermined period.

Figure 2:
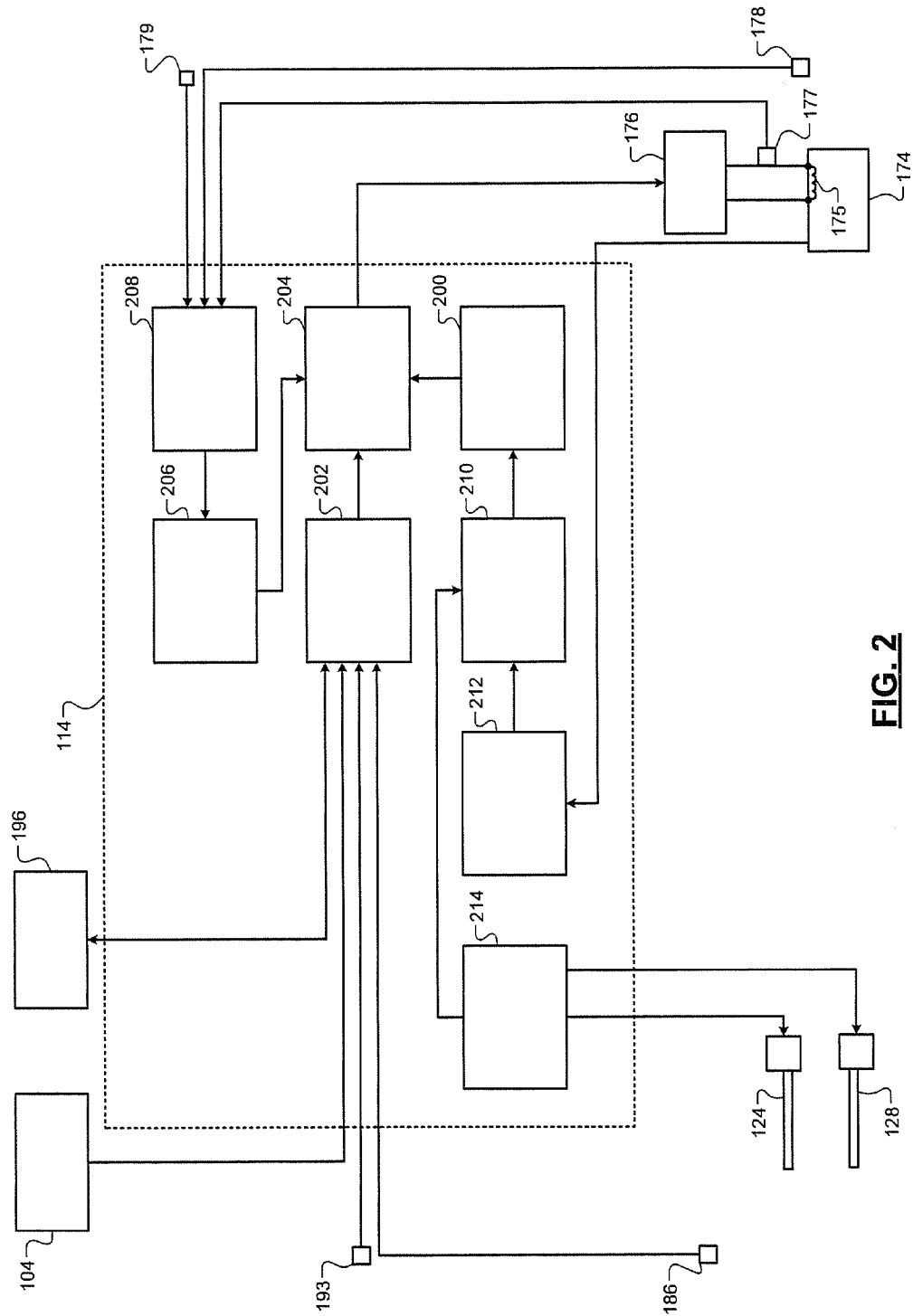
FIG. 2 is a functional block diagram of an example of an engine control system according to the principles of the present disclosure.

Referring now to FIG. 2, the ECM 114 includes a reactive cycling module 200, a proactive cycling module 202, and a heater control module 204. The reactive cycling module 200 commands the heater control module 204 to apply a heat cycle based on the response time of the oxygen sensor 174. The proactive cycling module 202 commands the heater control module 204 to apply a heat cycle based on engine operating conditions and/or vehicle mileage. The heater control module 204 applies a heat cycle by heating the oxygen sensor 174 to a predetermined temperature and/or for a predetermined period. The heater control module 204 heats the oxygen sensor 174 by controlling the power supply 176 to supply power to the heating element 175.

The reactive cycling module 200 commands the heater control module 204 to apply a heat cycle when the response time of the oxygen sensor 174 is greater than a predetermined time. The reactive cycling module 200 receives the response time of the oxygen sensor 174 from a response time determination module 210. The response time determination module 210 determines the response time of the oxygen sensor 174 based on an A/F ratio received from an A/F ratio determination module 212. The A/F ratio determination module 212 determines the A/F ratio based on an oxygen level received from the oxygen sensor 174.

The oxygen sensor 174 may output a voltage indicating the oxygen level in exhaust gas exiting the engine 102 of FIG. 1. The A/F ratio determination module 212 may receive the output voltage from the oxygen sensor 174 and may determine the A/F ratio based on the output voltage received. For example, the A/F ratio determination module 212 may determine that the A/F ratio is lean when the output voltage is 0.3 volts (V). In another example, the A/F ratio determination module 212 may determine that the A/F ratio is rich when the output voltage is 0.6 V.

The response time determination module 210 determines the response time of the oxygen sensor 174 based on when the A/F ratio is adjusted and when the oxygen sensor 174 responds to the adjustment. The response time determination module 210 determines when the A/F ratio is adjusted based on an input received from an A/F ratio control module 214. The A/F ratio control module 214 may adjust the A/F ratio via fuel injection and/or throttle control. The response time determination module 210 determines when the oxygen sensor 174 responds based on the A/F ratio received from the A/F ratio determination module 212. For example, the response time determination module 210 may determine that the oxygen sensor 174 responds to an adjustment from lean to rich when the A/F ratio determination module 212 outputs a rich A/F ratio.

The catalytic converter 172 of FIG. 1 may be most efficient at reducing emissions when the A/F ratio is maintained near stoichiometric. Thus, other than during special conditions, such as when a tow-haul mode is selected, the A/F ratio may be adjusted using closed-loop control with the oxygen sensor 174 providing feedback. During closed-loop control of the A/F ratio, the A/F ratio may be continuously dithered by a small percentage (e.g., 2 percent) from rich to lean and from lean to rich. As the A/F ratio is dithered, there may be a time lag from when the A/F ratio is adjusted by the A/F ratio control module 214 to when the A/F ratio indicated by the oxygen sensor 174 reflects this adjustment. This time lag is the response time of the oxygen sensor 174. A typical response time of the oxygen sensor 174 may be approximately 30 milliseconds (ms).

The reactive cycling module 200 may command the heater control module 204 to apply a heat cycle to the oxygen sensor 174 when the response time of the oxygen sensor 174 is greater than a predetermined time. The predetermined time may be approximately 1.5 times the acceptable limit according to emissions standards. For example, the acceptable limit may be 100 ms, and the predetermined time may be 150 ms. In another example, the predetermined time may be between about 100 ms and about 200 ms. The reactive cycling module 200 may command the heater control module 204 to apply a heat cycle by sending a control signal to the heater control module 204.

As discussed above, the proactive cycling module 202 commands the heater control module 204 to apply a heat cycle to the oxygen sensor 174 based on engine operating conditions and vehicle mileage. The engine operating conditions may include whether the engine 102 is started, whether the engine is about to be started, and the total amount of air that has passed through the exhaust system 134 of FIG. 1 (i.e., the accumulated airflow).

The proactive cycling module 202 may determine the vehicle mileage based on the wheel speed received from the wheel speed sensor 193 and the diameter of the corresponding wheel. The proactive cycling module 202 may determine when the engine 102 is started by a driver based on the driver input received from the driver input module 104. The proactive cycling module 202 may determine when the engine 102 is started automatically or is about to be started automatically, such as may occur in a start/stop hybrid, based on an input received from the hybrid control module 196.

The proactive cycling module 202 may determine the accumulated airflow based on the mass air flow received from the MAF sensor 186. The proactive cycling module 202 may determine the accumulated airflow based on values of the mass air flow and a period corresponding to the values. For example, the mass air flow may have a first value during a first period and a second value during a second period. The proactive cycling module 202 may determine the accumulated airflow for the first and second periods based on the products of the first and second values and the first and second periods, respectively.

The proactive cycling module 202 may periodically initiate a heat cycle based on the engine operating conditions and the vehicle mileage. The proactive cycling module 202 may initiate a heat cycle one or more times each time that the engine 102 is started or is about to be started. For example, the proactive cycling module 202 may initiate a heat cycle when a driver starts the engine 102, when the engine 102 is started automatically, or when the engine 102 is about to be started automatically.

When the engine 102 is started, water may be present in the exhaust system 134 until the exhaust system 134 reaches a certain temperature, which is typically about 54° C. If the oxygen sensor 174 is heated before this, water condensing on the inside walls of the exhaust system 134 may contact the ceramic element in the oxygen sensor 174, causing water shock of the ceramic element. Thus, the proactive cycling module 202 may refrain from initiating a heat cycle when the engine 102 is started until the exhaust system 134 reaches a predetermined temperature or until a predetermined period has elapsed.

The proactive cycling module 202 may initiate a heat cycle one or more times each time that the accumulated airflow increases by a predetermined mass. The predetermined mass may be determined based on testing conducted to determine the relationship between the accumulated airflow and the deposit buildup on the oxygen sensor 174. The predetermined mass may be selected to ensure that the deposit buildup on the oxygen sensor 174 does not diminish the performance of the oxygen sensor 174 below an acceptable level. For example, the predetermined mass may be approximately 1 million grams of air.

The proactive cycling module 202 may initiate a heat cycle one or more times each time that the vehicle mileage increases by a predetermined mileage. For example, the proactive cycling module 202 may initiate a heat cycle once for every 1,000 miles traveled by a vehicle.

The heater control module 204 applies a heat cycle to the oxygen sensor 174 when a heat cycle is initiated by either the reactive cycling module 200 or the proactive cycling module 202. The heater control module 204 may apply a heat cycle by heating the oxygen sensor 174 to a predetermined temperature and/or for a predetermined period. The predetermined temperature and the predetermined period may be determined through testing. The testing may be conducted to determine the relationship between temperatures of the oxygen sensor 174, time periods corresponding to the temperatures, and combustion of deposits on the oxygen sensor 174.

During normal operation, the heater control module 204 may control the heating element 175 of the oxygen sensor 174 to a temperature using a typical control range that is between 600° C. and 800° C. When applying a heat cycle, the heater control module 204 may heat the oxygen sensor 174 to the predetermined temperature, which may be greater than the typical control range. For example, the predetermined temperature may be greater than 800° C. (e.g., approximately 900° C.), greater than 820° C., greater than 840° C., greater than 860° C., greater than 880° C., greater than 900° C., greater than 920° C., greater than 940° C., greater than 960° C., or greater than 980° C. Additionally or alternatively, the heater control module 204 may heat the oxygen sensor 174 for the predetermined period. For example, the predetermined period may be greater than 5 minutes (e.g., approximately 20 minutes).

The heater control module 204 may receive the temperature of the oxygen sensor 174 from a temperature determination module 206. The temperature determination module 206 determines the temperature of the oxygen sensor based on a resistance of the heating element 175 and a predetermined relationship between the resistance of the heating element 175 and the temperature of the oxygen sensor 174. This relationship may be represented in the form of an equation or a lookup table. The temperature determination module 206 may receive the resistance of the heating element 175 from the resistance determination module 208.

The resistance determination module 208 determines the resistance of the heating element 175 based on a voltage supplied to the heating element 175 and a current supplied to the heating element 175. The resistance determination module 208 may receive the current supplied to the heating element 175 from the current sensor 177. The resistance determination module 208 may assume that the voltage supplied to the heating element 175 is equal to the voltage in the engine system 100. The resistance determination module 208 may receive this voltage from the voltage sensor 179.

Figure 3:
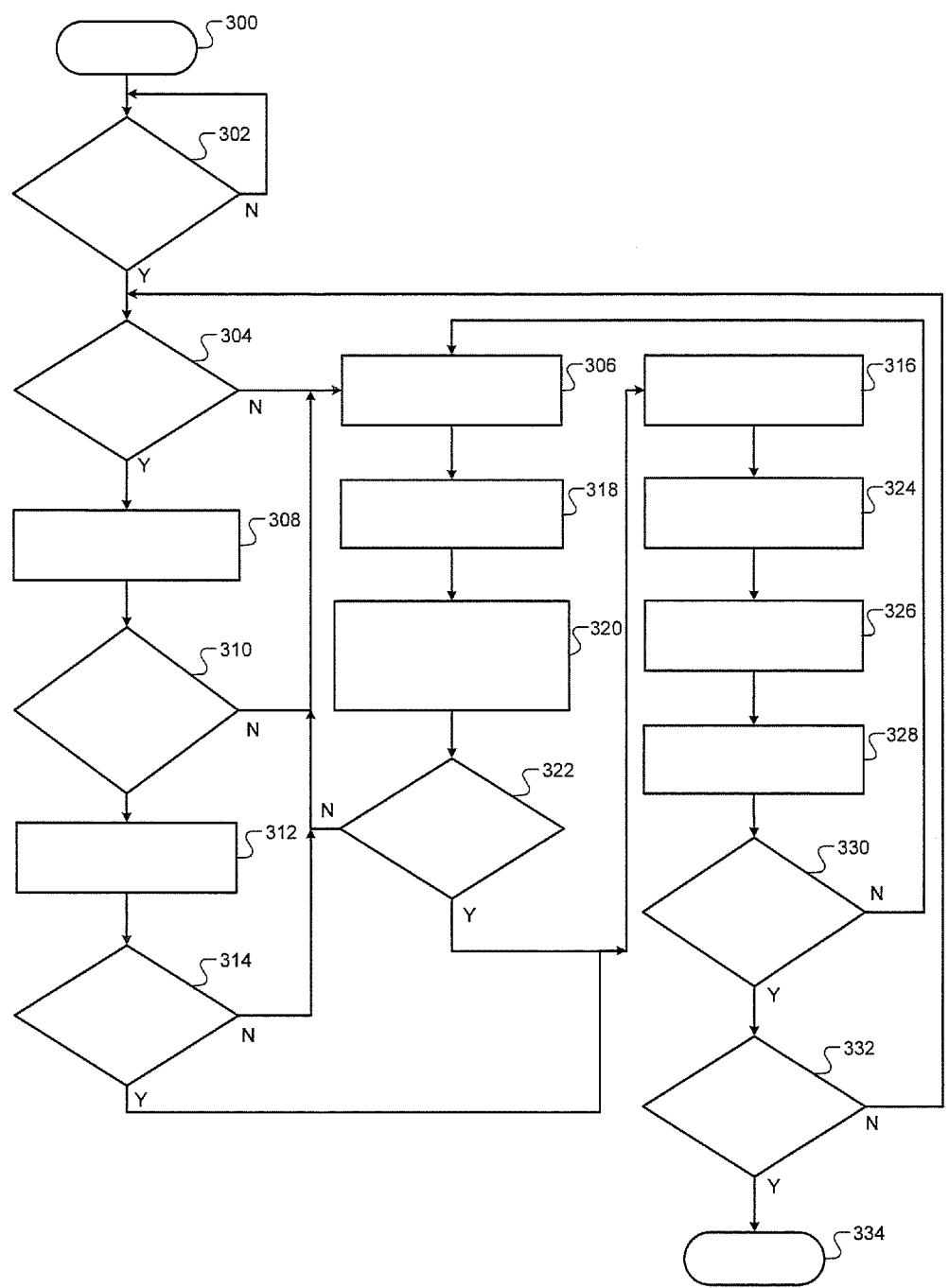
FIG. 3 is a flow chart illustrating a method of heating an oxygen sensor in an exhaust system in an engine according to the principles of the present disclosure.

Referring now to FIG. 3, a method for heating an oxygen sensor in an exhaust system of an engine may begin at 300. At 302, the method determines whether the engine is started or is about to be started. If 302 is false, the method continues to determine whether the engine is started or is about to be started. If 302 is true, the method continues at 304. At 304, the method determines whether an engine on period is less than a first period. If 304 is false, the method continues at 306. If 304 is true, the method continues at 308.

The oxygen sensor may be damaged if the oxygen sensor is heated while water is present in the exhaust system. Typically, water is present in an exhaust system until the exhaust system is heated to approximately 54° C. Thus, the first period may be predetermined through testing based on the amount of time required to heat the oxygen sensor with exhaust gas until water in the exhaust system is no longer present.

At 308, the method determines an accumulated airflow. The accumulated airflow is the total amount of air that has passed through the exhaust system over a period of time. The accumulated airflow may be determined based on a mass airflow indicated by a mass airflow sensor in an intake system of the engine. The method continues at 310 and determines whether the accumulated airflow is less than a predetermined mass. If 310 is false, the method continues at 306. If 310 is true, the method continues at 312.

The predetermined mass may be determined based on testing conducted to develop a relationship between the accumulated airflow and a deposit buildup on the oxygen sensor. The predetermined mass may correspond to a maximum allowable deposit buildup on the oxygen sensor. The maximum allowable deposit buildup on the oxygen sensor may correspond to a maximum allowable response time of the oxygen sensor.

At 312, the method determines a vehicle mileage. The method may determine the vehicle mileage based on wheel speeds indicated by a wheel speed sensor, the diameter of a wheel to which the wheel speed sensor is coupled, and the time periods corresponding to the wheel speeds. The method continues at 314 and determines whether the vehicle mileage is less than a predetermined mileage. If 314 is false, the method continues at 306. If 314 is true, the method continues at 316.

The predetermined mileage may be determined based on testing conducted to correlate the vehicle mileage and a buildup of deposits on the oxygen sensor. The predetermined mileage may correspond to a maximum allowable deposit buildup on the oxygen sensor. The maximum allowable deposit buildup on the oxygen sensor may correspond to a maximum allowable response time of the oxygen sensor.

At 306, the method determines a resistance of a heating element of the oxygen sensor. The method may determine the resistance of the heating element based on a current supplied to the heating element and a voltage supplied to the heating element. The current and the voltage may be measured at a location between a power supply and the heating element. Alternatively, the voltage and the current may be measured at other locations in the electrical system of the engine.

The method continues at 318 and determines the temperature of the oxygen sensor. The method may determine the temperature of the oxygen sensor based on a predetermined relationship between the resistance of the heating element and the temperature of the oxygen sensor. The predetermined relationship may be represented in the form of a lookup table or an equation.

The method continues at 320 and activates the heating element to heat the oxygen sensor to a predetermined temperature. The predetermined temperature may be determined based on testing conducted to determine the relationship between the temperature of the oxygen sensor and combustion of deposits on the oxygen sensor. The predetermined temperature is a temperature at which deposits on the oxygen sensor are combusted. The predetermined temperature may be greater than 800° C., greater than 820° C., greater than 840° C., greater than 860° C., greater than 880° C. (e.g., approximately 900° C.), greater than 900° C., greater than 920° C., greater than 940° C., greater than 960° C., or greater than 980° C.

At 322, the method determines whether a heating period is greater than a predetermined period. If 322 is false, the method returns to 306. If 322 is true, the method continues at 316.

The heating period is the period during which the oxygen sensor is heated to the predetermined temperature. The predetermined period may be determined based on testing conducted to determine the relationship between temperatures of the oxygen sensor, periods corresponding to the temperatures, and combustion of deposits on the oxygen sensor. The predetermined period may be greater than 5 minutes (e.g., approximately 20 minutes).

At 316, the method dithers the A/F ratio between rich and lean. The method may continuously dither the A/F ratio by a small percentage from rich to lean and from lean to rich during closed-loop control of the A/F ratio.

The method continues at 324 and monitors the oxygen level indicated by the oxygen sensor. The oxygen sensor may indicate the oxygen level by generating a voltage that indicates the oxygen level. The voltage may also indicate an A/F ratio of the engine. For example, a voltage of 0.3V may indicate a high oxygen level and a lean A/F ratio. In another example, a voltage of 0.6V may indicate a low oxygen level and a rich A/F ratio.

The method continues at 326 and determines an A/F ratio. The method may determine the A/F ratio based on the oxygen level indicated by the oxygen sensor. The method may determine the A/F ratio directly from the voltage generated by the oxygen sensor.

The method continues at 328 and determines the response time of the oxygen sensor. The response time of the oxygen sensor is the time lag between the time at which the A/F ratio is dithered to the time at which the A/F ratio indicated by the oxygen sensor reflects this dither. The method may continuously determine the response time of the oxygen sensor while the method is continuously dithering the A/F ratio.

The method continues at 330 and determines whether the response time is less than a predetermined time. If 330 is false, the method returns to 306. If 330 is true, the method continues at 332. The predetermined time may be a maximum response time of the oxygen sensor that enables closed-loop control of the A/F ratio to satisfy emission standards. For example, the predetermined time may range from 100 ms to 200 ms.

At 332, the method determines whether the engine is stopped. If 332 is false, the method returns to 304. If 332 is true, the method ends at 334.

In this manner, the method may employ a proactive approach and/or a reactive approach to maintain the response time of the oxygen sensor within an acceptable level. In either approach, the method may continuously run various checks and apply a heat cycle to the oxygen sensor when the various checks satisfy predetermined criteria. In the proactive approach, the various checks may look at engine operating conditions and vehicle mileage. In the reactive approach, the various checks may look at the response time of the oxygen sensor.

Although the method illustrated in FIG. 3 includes various checks for both the reactive approach and the proactive approach, each of these approaches may be executed independently and some or all of the various checks in each approach may be omitted. In addition, the various checks may be executed in an order that is different than that shown in FIG. 3.

Figure 4:
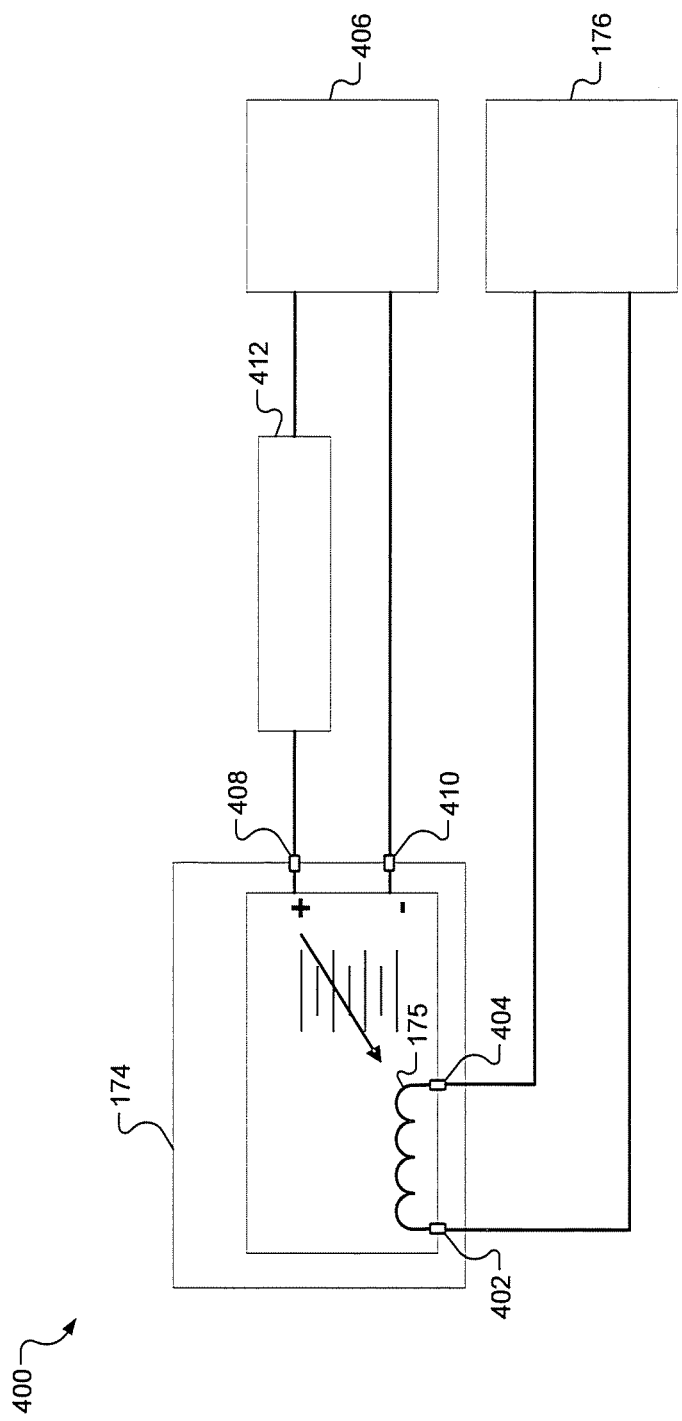
FIG. 4 is a functional block diagram of a test system for evaluating a control system and method for heating an oxygen sensor according to the principles of the present disclosure.

Referring now to FIG. 4, a test system 400 is shown. The test system 400 may be used to evaluate the effectiveness of a control system and method for heating an oxygen sensor according to the principles of the present disclosure. The test system 400 includes the oxygen sensor 174, the heating element 175, and the power supply 176. However, various oxygen sensors, heating elements, and power supplies may be employed in the test system 400. The power supply 176 may be controlled to activate the heating element 175, and thereby heat the oxygen sensor 174. The power supply 176 is connected to the heating element 175 via heater terminals 402, 404.

A power supply 406 may be connected to signal terminals 408, 410 of the oxygen sensor 174. The power supply 406 may be controlled to supply power to the signal terminals 408, 410. The current supplied from the power supply 406 to the oxygen sensor 174 may be measured using an ammeter or current sensor 412.

When the oxygen sensor 174 is in an exhaust system, as in FIG. 1, the potential difference between the signal terminals 408, 410 is proportional to the amount of oxygen diffused through the oxygen sensor 174. Oxygen ions flowing through pores in the sensor 174 generate a current which results in the potential difference between the signal terminals 408, 410. The signal terminals 408, 410 may be connected to a controller to provide the potential difference between the signal terminals 408, 410 to the controller. The controller may then determine the oxygen level in an exhaust gas and/or an A/F ratio based on the potential difference between the signal terminals 408, 410.

In contrast, in the test system 400, power is supplied to the signal terminals 408, 410 and the current passing through the oxygen sensor 174 is measured to determine the ability of the oxygen sensor 174 to diffuse oxygen. The current passing through the oxygen sensor 174 may be referred to as a pumping current. The signal terminal 410 may be an input terminal, the signal terminal 408 may be an output terminal, and the pumping current may be measured using the current sensor 412.

As the ability of the oxygen sensor to diffuse oxygen decreases, the response time of the oxygen sensor 174 increases. Thus, since the pumping current indicates the ability of the oxygen sensor 174 to diffuse oxygen, the pumping current also indicates the response time of the oxygen sensor 174.

Equation 1, listed below, provides the relationship between the pumping current and the ability of the oxygen sensor 174 to diffuse oxygen.

$$Ip=(4*F*D*Q*C)/L \quad \text{Equation 1}$$

In Equation 1, Ip represents the pumping current, F represents the Faraday constant, D represents the diffusion coefficient of the oxygen sensor 174, Q represents the diffusion area of the oxygen sensor 174, C represents the oxygen concentration in the gas passing through the oxygen sensor 174, and L represents the diffusion length.

The diffusion coefficient may vary based on the type of ceramic element used in the oxygen sensor 174. The diffusion coefficient may also vary based on the number of pores that are plugged or clogged with deposits from exhaust gas passing through the oxygen sensor 174. The diffusion area may be the area of the ceramic element and the oxygen sensor 174. Since the test system 400 may be used when the oxygen sensor 174 is in an open area environment, the oxygen concentration may simply be the concentration of oxygen in air (e.g., 22 percent). The diffusion length may be the thickness of the ceramic element and the oxygen sensor 174.

The pumping current indicates the ability of the oxygen sensor 174 to diffuse oxygen (i.e., flow oxygen ions through a ceramic element). As pores in the ceramic element of the oxygen sensor 174 become plugged, the diffusion coefficient decreases, and therefore the pumping current decreases. Conversely, as deposits in the pores of the oxygen sensor 174 are combusted and oxygen ions are allowed to flow once again through the pores, the diffusion coefficient increases, and therefore the pumping current increases. Since the ability of the oxygen sensor 174 to diffuse oxygen is directly related to the response time of the oxygen sensor, the pumping current is directly related to the response time of the oxygen sensor.

Figure 5:
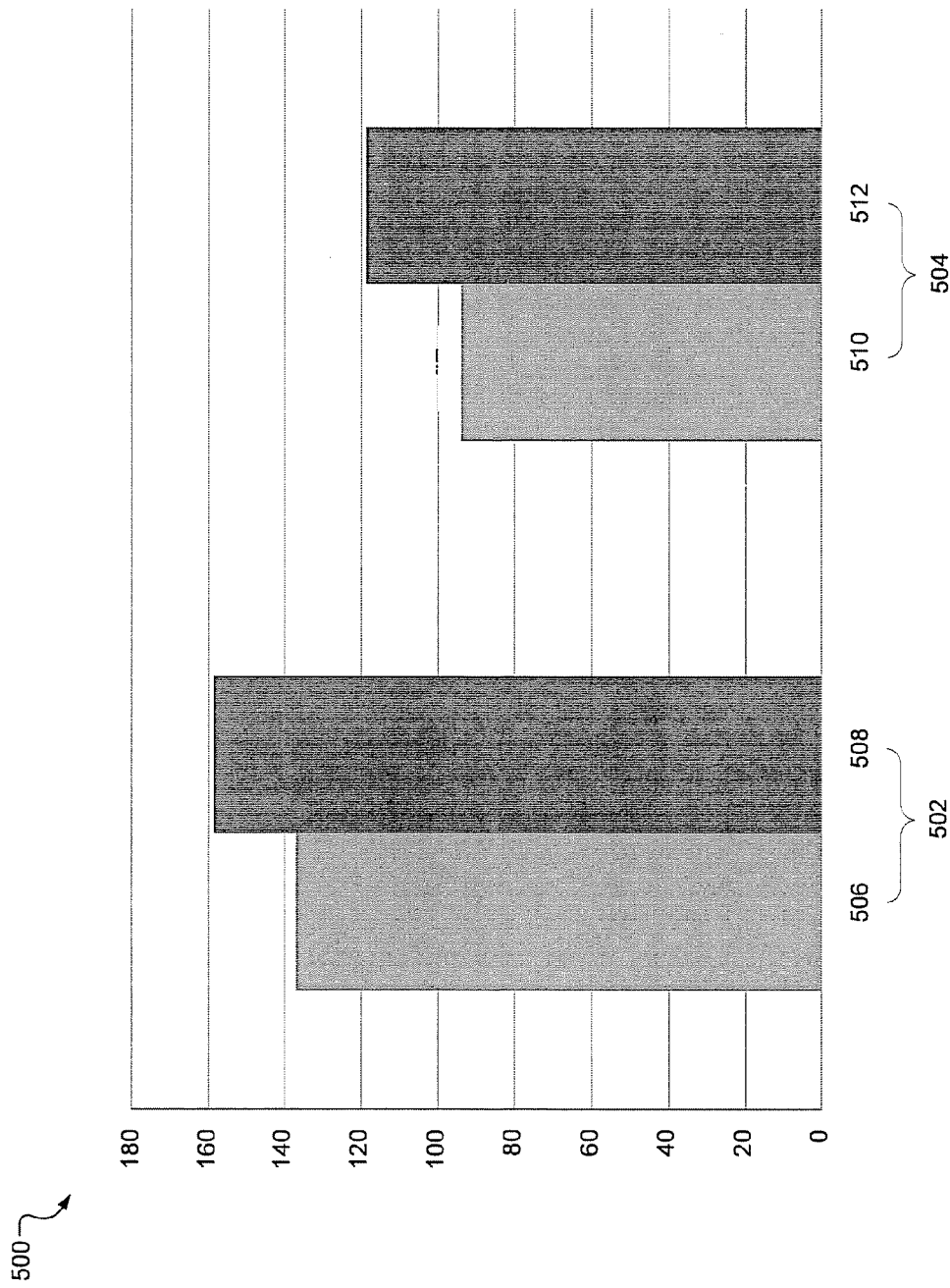
FIG. 5 is a graph illustrating the effectiveness of a control system and method for heating an oxygen sensor according to the principles of the present disclosure.

Referring to FIG. 5, a graph 500 illustrates the pumping currents of two oxygen sensors before and after a heat cycle is applied. The data shown in the graph 500 may be obtained using the test system 400 shown in FIG. 4.

The pumping current of a first sensor before and after applying a heat cycle is shown at 502, and the pumping current of a second sensor before and after applying a heat cycle is shown at 504. The pumping current of the first sensor before applying a heat cycle is shown at 506 and the pumping current of the first sensor after applying a heat cycle at 508. The pumping current of the second sensor before applying a heat cycle is shown at 510 and the pumping current of the second sensor after applying a heat cycle is shown at 512.

Before obtaining the results shown in the graph 500, the first sensor and the second sensor were subjected to 150,000 equivalent miles through accelerated testing. When obtaining the results shown in the graph 500, the pumping currents of the sensors were measured, a heat cycle was applied to the sensors, and the pumping currents of the sensors were measured again. A heat cycle was applied to the first and second sensors by increasing the temperature of the first and second sensors to 900° C. for 20 minutes.

As shown in the graph 500, the pumping current of the first sensor was approximately 137 milliamps (mA) before a heat cycle was applied, and the pumping current of the first sensor was approximately 159 mA after a heat cycle was applied. Thus, the pumping current of the first sensor increased by approximately 22 mA after a heat cycle was applied to the first sensor. This increase in the pumping current of the first sensor after applying a heat cycle to the first sensor indicates that applying a heat cycle decreases the response time of the first sensor.

Applying a heat cycle to the second sensor yielded similar results by increasing the pumping current of the second sensor. As shown in the graph 500, the pumping current of the second sensor was 94 mA before a heat cycle was applied, and the pumping current of the second sensor was 119 mA after a heat cycle was applied. Thus, the pumping current of the second sensor increased by approximately 20 mA after a heat cycle was applied. As with the first sensor, this increase in the pumping current of the second sensor after applying a heat cycle to the second sensor indicates that applying a heat cycle to the second sensor decreases the response time of the second sensor.

Therefore, the graph 500 shows that applying a heat cycle to an oxygen sensor as described in the present disclosure decreases the response time of the oxygen sensor, thus improving the performance of the oxygen sensor.

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

What is claimed is:

1. A system, comprising:
   an oxygen sensor configured to be disposed in an exhaust system of an engine and including a heating element;
   a first electronic circuit configured to determine a temperature of the oxygen sensor;
   a second electronic circuit configured to apply a heat cycle to combust deposits on the oxygen sensor by activating the heating element of the oxygen sensor to increase the temperature of the oxygen sensor to greater than 800 degrees Celsius;
   a third electronic circuit configured to initiate the heat cycle based on at least one of a vehicle mileage and a mass airflow in an intake system of the engine; and
   a power supply, wherein the second electronic circuit activates the heating element by controlling the power supply to supply power to the heating element.

2. The system of claim 1, wherein the second electronic circuit is configured to apply the heat cycle for a predetermined period.

3. The system of claim 1, wherein the third electronic circuit is configured to initiate the heat cycle based on the vehicle mileage.

4. The system of claim 1, wherein the third electronic circuit is configured to initiate the heat cycle based on the mass airflow in the intake system of the engine.

5. The system of claim 1, wherein the third electronic circuit is configured to initiate the heat cycle when the engine is started.

6. The system of claim 1, wherein the first, second, and third electronic circuits include at least one of an Application Specific Integrated Circuit, a combinational logic circuit, a field programmable gate array, a processor, and memory.

7. The system of claim 1, wherein the first electronic circuit is configured to determine the temperature of the oxygen sensor based on a resistance of the heating element.

8. The system of claim 7, further comprising a fourth electronic circuit configured to determine the resistance of the heating element based on a voltage and a current that are supplied to the heating element.

9. The system of claim 1, wherein the third electronic circuit is configured to initiate the heat cycle based on a response time of the oxygen sensor.

10. The system of claim 9, further comprising a fourth electronic circuit configured to determine the response time of the oxygen sensor based on an air/fuel (A/F) ratio of the engine.

11. The system of claim 10, further comprising a fifth electronic circuit configured to determine the A/F ratio of the engine based on an oxygen level indicated by the oxygen sensor.

12. A method, comprising:
    determining a temperature of an oxygen sensor in an exhaust system of an engine;
    initiating a heat cycle based on at least one of a vehicle mileage and a mass airflow in an intake system of the engine; and
    upon initiation of the heat cycle, increasing the temperature of the oxygen sensor to greater than 800 degrees Celsius using a heating element of the oxygen sensor to combust deposits on the oxygen sensor.

13. The method of claim 12, further comprising applying the heat cycle for a predetermined period.

14. The method of claim 12, further comprising activating the heating element by controlling a power supply to supply power to the heating element.

15. The method of claim 12, further comprising determining the temperature of the oxygen sensor based on a resistance of the heating element.

16. The method of claim 15, further comprising determining the resistance of the heating element based on a voltage and a current that are supplied to the heating element.

17. The method of claim 12, further comprising initiating the heat cycle based on the vehicle mileage.

18. The method of claim 17, further comprising initiating the heat cycle based on the mass airflow in the intake system of the engine.

19. The method of claim 17, further comprising initiating the heat cycle based on when the engine is started.

20. The method of claim 12, further comprising initiating the heat cycle based on a response time of the oxygen sensor.

21. The method of claim 20, further comprising determining the response time of the oxygen sensor based on an air/fuel (A/F) ratio of the engine.

22. The method of claim 21, further comprising determining the A/F ratio of the engine based on an oxygen level indicated by the oxygen sensor.

* * * * *

UNITED STATES PATENT AND TRADEMARK OFFICE
CERTIFICATE OF CORRECTION

PATENT NO. : 9,146,210 B2  
APPLICATION NO. : 12/917868  
DATED : September 29, 2015  
INVENTOR(S) : Gibson et al.

Page 1 of 1

It is certified that error appears in the above-identified patent and that said Letters Patent is hereby corrected as shown below:

Title Page, item "(76)" should read item -- (75) --.

Title Page, Item [73] Assignee, insert the following:
--GM Global Technology Operations LLC, Detroit, MI (US)--

Signed and Sealed this
Twenty-first Day of June, 2016

Michelle K. Lee
*Director of the United States Patent and Trademark Office*